United States Patent
Bottomley et al.

(10) Patent No.: US 10,292,615 B2
(45) Date of Patent: May 21, 2019

(54) METHODS AND APPARATUS FOR ACCELERATED, MOTION-CORRECTED HIGH-RESOLUTION MRI EMPLOYING INTERNAL DETECTORS OR MRI ENDOSCOPY

(71) Applicant: The Johns Hopkins University, Baltimore, MD (US)

(72) Inventors: Paul Bottomley, Baltimore, MD (US); Yi Zhang, Baltimore, MD (US); Shashank S. Hegde, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 1101 days.

(21) Appl. No.: 14/424,863

(22) PCT Filed: Sep. 20, 2013

(86) PCT No.: PCT/US2013/061015
§ 371 (c)(1),
(2) Date: Feb. 27, 2015

(87) PCT Pub. No.: WO2014/047498
PCT Pub. Date: Mar. 27, 2014

(65) Prior Publication Data
US 2015/0257675 A1   Sep. 17, 2015

Related U.S. Application Data

(60) Provisional application No. 61/703,674, filed on Sep. 20, 2012, provisional application No. 61/808,485, filed on Apr. 4, 2013.

(51) Int. Cl.
*A61B 5/00* (2006.01)
*A61B 5/055* (2006.01)
(Continued)

(52) U.S. Cl.
CPC ............ *A61B 5/055* (2013.01); *A61B 5/7203* (2013.01); *G01R 33/285* (2013.01);
(Continued)

(58) Field of Classification Search
CPC .................................................. G01R 33/5611
See application file for complete search history.

(56) References Cited

U.S. PATENT DOCUMENTS

| 4,766,381 A | 8/1988 | Conturo et al. |
| 5,699,801 A | 12/1997 | Atalar et al. |

(Continued)

FOREIGN PATENT DOCUMENTS

| WO | WO-01/073461 A2 | 10/2001 |
| WO | WO-2008/082661 A2 | 7/2008 |

(Continued)

OTHER PUBLICATIONS

Block et. al, Magn Reson Med 2007; 57: 1086-1098.
(Continued)

*Primary Examiner* — Joseph M Santos Rodriguez
(74) *Attorney, Agent, or Firm* — Venable LLP; Henry J. Daley

(57) ABSTRACT

A method of internal MRI employing at least one active internal MRI detector located within a sample of interest. The method includes applying an MRI pulse sequence to the sample of interest. The MRI pulse sequence includes spatial encoding projections. The method further includes receiving MRI signals at the active internal MRI detector and reconstructing at least one MRI image from the MRI signals using an error minimizing algorithm. The MRI pulse sequence provides an increase in an acquisition speed when reconstructing the at least one MRI image by sparsely under-sampling an image k-space in at least one dimension.

25 Claims, 16 Drawing Sheets

(51) Int. Cl.
*G01R 33/34* (2006.01)
*G01R 33/561* (2006.01)
*G01R 33/28* (2006.01)
*G01R 33/48* (2006.01)
*G01R 33/56* (2006.01)
*G01R 33/565* (2006.01)

(52) U.S. Cl.
CPC ... *G01R 33/34084* (2013.01); *G01R 33/4818* (2013.01); *G01R 33/56* (2013.01); *G01R 33/561* (2013.01); *G01R 33/34038* (2013.01); *G01R 33/4824* (2013.01); *G01R 33/56509* (2013.01)

(56) References Cited

U.S. PATENT DOCUMENTS

| | | | |
|---|---|---|---|
| 5,928,145 | A | 7/1999 | Ocali et al. |
| 7,653,426 | B2 | 1/2010 | Yatsuo et al. |
| 2007/0096732 | A1 | 5/2007 | Samsonov et al. |
| 2010/0256480 | A1* | 10/2010 | Bottomley ............ G01R 33/285 600/411 |
| 2011/0084693 | A1* | 4/2011 | Kholmovski ...... G01R 33/5611 324/310 |

FOREIGN PATENT DOCUMENTS

| | | |
|---|---|---|
| WO | WO-2011-087847 A2 | 7/2011 |
| WO | WO-2011-116785 A1 | 9/2011 |
| WO | WO-2012-011583 A1 | 1/2012 |

OTHER PUBLICATIONS

Candes et al., An introduction to compressive sampling. Signal Processing Magazine, IEEE, 25 (2008) 21-30.
Candes et al., Robust uncertainty principles: Exact signal reconstruction from highly incomplete frequency information. IEEE Trans Inf Theor 2006; 52: 489-509.
Donoho DL., Compressed sensing. IEEE Trans Inf Theor. 2006; 52:12891306.
Gamper et al., Compressed sensing in dynamic MRI. Magn Reson Med 2008; 59: 365-373.
Ginefri et al., "Implanted, inductively-coupled, radiofrequency coils fabricated flexible polymeric material: Application to in vivio rat brain MRI at 7T," J Magn Reson. 2012, 224C: 61-70.
Hegde et al., Accelerated, motion-corrected high-resolution intravascular MRI at 3T. Proc ISMRM 2013 (In press, Apr. 2013).
Jung et al., Improved k-t BLASK and k-t SENSE using FOCUSS. Phys Med Biol 2007; 52: 3201-3226.
Jung et al., Radial k-t FOCUSS for High-Resolution Cardiac Cine MRI. Magn Reson Med 2010; 63:68-78.
Lauterbur PC., "Image Formation by Induced Local Interactions: Examples Employing Nuclear Magnetic Resonance"; Nature, 1973; 242: 190-191.
Lustig et. al, Magn Reson Med, 2007;58(6):1182-1195.
Ocali et al., "Intravascular magnetic resonance imaging using a loopless catheter antenna", Magn. Reson/ Med. 1997; 37:112-118.
Qian et al., "High-resolution intravascular magnetic resonance quantification of atherosclerotic plaque at 3T", Journal of Cardiovascular Magnetic Resonance, 2012: 14:20, doi:10.1186/1532-429X-14-20.
Qiu et al., "Development of a 0.0145-inch magnetic resonance imaging guidewire," Magn Reson Med. 2005; 53(4): 986-90.
Rudin et al., Nonlinear total variation based noise removal algorithms. Physica D: Nonlinear Phenomenn 1992; 60: 259-268.
Sathyanarayana et al., "MRI endoscopy using intrinsically localized probes", Med Phys 2009; 36: 908-919.
Sathyanarayana et al., "Towards real-time intravascular endoscopic MRI", J Am Coll Cardiol Img 2010; 3: 1158-1165.
U.S. Appl. No. 61/703,674, filed Sep. 20, 2012.
Usman et al., Motion Corrected Compressed Sensing for Free-Breathing Dynamic Cardiac MRI. Magn Reson Med (in press: Aug. 2012: DOI: 10.1002/mrm.24463).
International Search Report and Written Opinion of PCT/US2013/061015.

* cited by examiner

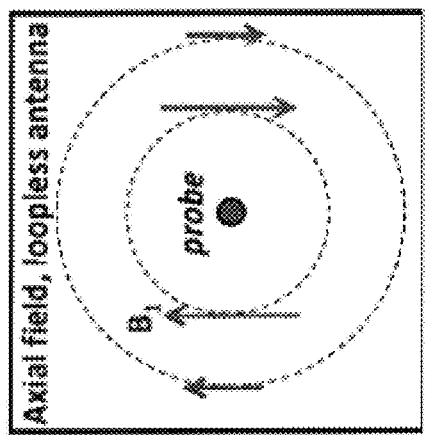
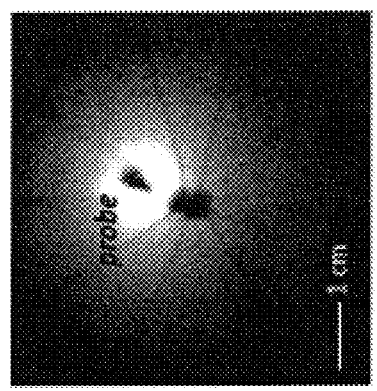
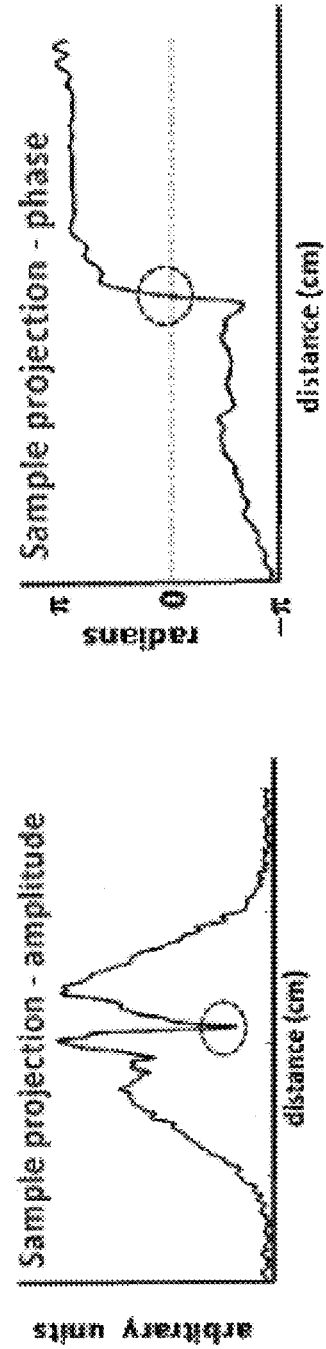
Figs. 12A-12D

METHODS AND APPARATUS FOR ACCELERATED, MOTION-CORRECTED HIGH-RESOLUTION MRI EMPLOYING INTERNAL DETECTORS OR MRI ENDOSCOPY

CROSS REFERENCE TO RELATED APPLICATIONS

This is a national stage application under 35 U.S.C. § 371 of PCT/US2013/061015filed Sep. 20, 2013, the entire contents of which are incorporated herein by reference and this Application claims the benefit of U.S. Provisional Patent Application 61/703,674, filed Sep. 20, 2012, titled "MOTION-INSENSITIVE, PROJECTION-BASED MRI ENDOSCOPY METHOD", as well as U.S. Provisional Patent Application 61/808,485, filed Apr. 4, 2013, titled "METHODS AND APPARATUS FOR ACCELERATED, MOTION-CORRECTED HIGH-RESOLUTION MRI EMPLOYING INTERNAL DETECTORS OR MRI ENDOSCOPY", both of which are incorporated by reference herein in their entirety.

FEDERAL FUNDING

This invention was made with Government support of Grant Nos. EB007829 and HL090728awarded by The National Institutes of Health (NIH). The Government has certain rights in the invention.

BACKGROUND

1. Field of Invention

The field of the currently claimed embodiments of this invention relates to magnetic resonance imaging (MRI) systems and methods, and more particularly to MRI systems and methods that include motion correction and/or accelerated processing for increased frame rates.

2. Discussion of Related Art

The advantageous use of magnetic resonance technology in providing safe, rapid images of a patient has long been known. It has also been known to employ resonance technology in producing chemical shift spectra to provide information regarding the chemical content of a material.

In a general sense, magnetic resonance imaging involves providing bursts of radio frequency energy on a specimen positioned within a main magnetic field in order to induce responsive emission of magnetic radiation from the hydrogen nuclei or other nuclei. The emitted signal may be detected in such a manner as to provide information as to the intensity of the response and the spatial origin of the nuclei emitting the responsive magnetic resonance signal.

In general, imaging may be performed in a slice or plane or multiple planes or three-dimensional volume with information corresponding to the responsively emitted magnetic radiation being received and conveyed to a computer which stores the information in the form of numbers or data corresponding to the intensity and phase of the signal. The pixel value may be established in a computer by employing Fourier Transformation (FT) which converts the signal amplitude and phase as a function of time to signal as a function of frequency, which translates to spatial position within the volume. The signals may be stored in the computer and may be delivered with or without enhancement to a video screen display, such as a cathode-ray tube, for example, wherein the image created by the computer output will be presented through black and white presentations varying in intensity, or color presentations varying in hue and intensity. See, generally, U.S. Pat. No. 4,766,381.

Recently, MRI technology has been used in connection with endoscopes, where a stream of images is provided from the viewpoint of an MRI probe introduced internally into the imaging volume[1]. For example, the probe may be moved through orifices, or blood vessels, or tissues in a human body with the intrinsic high sensitivity to pathology that characterizes MRI. However, the probe advancement has been limited by scan time which renders the images sensitive to motion artefact.

Current speeds for intravascular (IV) MRI and MRI endoscopy[1] are limited to ~2 frames/s at 3T, although it will be appreciated that higher and lower frame rates are often desirable to enhance particular aspects of the responsive signals, such as image contrast or flow sensitivity etc. In any case it will be appreciated that high-resolution (e.g. ~50-500 µm) images may be susceptible to degradation by physiological and random motions when their amplitudes are of the order of mm at time-frames shorter than the scan period.

Compressed sensing has been previously proposed and implemented to speed up conventional MRI and angiography[2-7]. It is also used in other image applications involving data and image compression. However, it has not been adapted for use in MRI endoscopy with either radial projection or Cartesian MRI pulse sequences, nor in conjunction with internal MRI detectors.

Therefore, there remains a need for improved MRI systems and methods for motion correction and/or accelerated processing for increased frame rates.

SUMMARY

A method of internal MRI employing at least one active internal MRI detector located within a sample of interest according to an embodiment of the current invention includes applying an MRI pulse sequence to the sample of interest which includes the at least one active internal MRI detector. The MRI pulse sequence includes spatial encoding projections. The method further includes receiving MRI signals at the at least one active internal MRI detector and reconstructing at least one MRI image from the MRI signals using an error minimizing algorithm. The MRI pulse sequence provides an increase in an acquisition speed when reconstructing the at least one MRI image by sparsely under-sampling an image k-space in at least one dimension.

An MRI scanner according to an embodiment of the current invention includes a magnet system, an MRI detection system, and a data acquisition system. The data acquisition system is configured to perform accelerated high-resolution internal MRI with at least one active internal MRI detector, and an MRI pulse sequence in which an image projection is acquired in at least one spatial dimension/ The at least one image is reconstructed by using an error minimization algorithm, and the MRI pulse sequence provides an increase in an acquisition speed when reconstructing said at least one image by sparsely under-sampling an image k-space in at least one dimension.

An active MRI detector according to an embodiment of the current invention can perform internal MRI when employed with an MRI pulse sequence in which an image projection is acquired in at least one spatial dimension. The MRI properties of the detector are such that in at least one projection the MRI signal the detector exhibits at least one singularity in the vicinity of its location, and the singularity involves at least one of: the sensitivity of the detector undergoes a transition from substantially an MRI signal maximum immediately adjacent to said MRI detector to substantially a signal void at the location of the detector itself is substantially voided, or the phase of the detector undergoes a substantial reversal from at least at one location adjacent to the said MRI detector as compared to a location diametrically opposite to the at least one adjacent location.

A method of internal MRI employing at least one active internal MRI detector located within a sample of interest according to an embodiment of the current invention includes applying an MRI pulse sequence to the sample of interest which includes the at least one active internal MRI detector. The MRI pulse sequence excites at least one spatial projection of the sample. The method further includes receiving MRI signals at the at least one active internal MRI detector; and reconstructing at least one MRI image from the MRI signals. In the least one spatially-encoding projection, an MRI signal of the detector exhibits at least one singularity in a vicinity of a location of said internal MRI detector, a location of the singularity is detected in said at least one projection using a detection algorithm, and the projection is shifted to the center of the MRI field of view prior to image reconstruction.

BRIEF DESCRIPTION OF THE DRAWINGS

Further objectives and advantages will become apparent from a consideration of the description, drawings, and examples.

FIG. 12A shows an image of a probe.

FIG. 12B shows an axial field of a loopless antenna.

FIG. 12C shows a sample projection with an amplitude crater at the probe.

FIG. 12D shows a sample projection with a phase reversal at the probe.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

Figure 1:
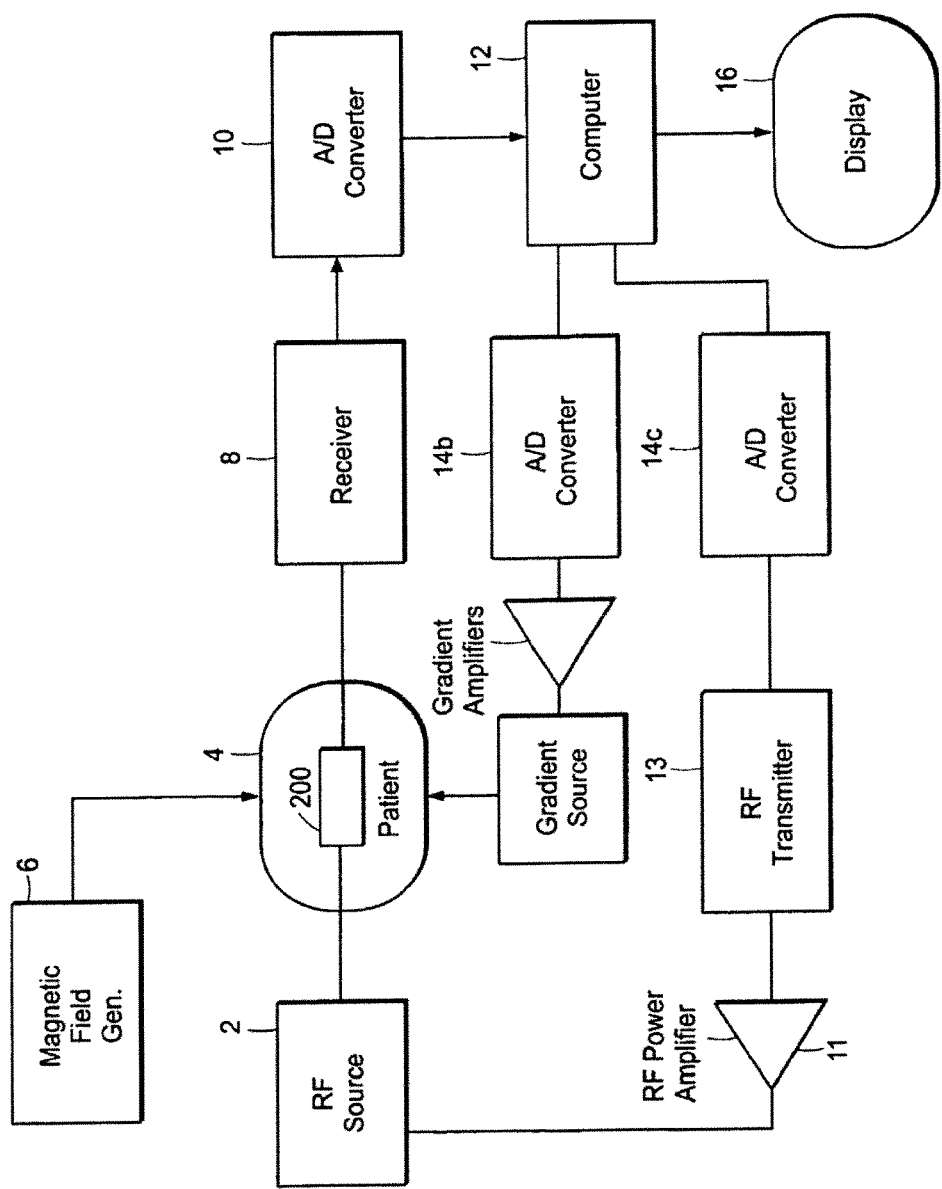
FIG. 1 shows an example embodiment of an MRI system.

The present invention pertains to MRI internal detectors on MRI endoscopy providing a continuous stream of images from the viewpoint of an internal MRI probe, such as described in U.S. Pat. No. 5,699,801, U.S. Patent Publication No. 2010/0256480, and Sathyanarayana S, Bottomley P A, "MRI endoscopy using intrinsically localized probes", Med Phys 2009; 36: 908-919 (PMCID: PMC2673676), which are incorporated by reference herein. Referring now to the various figures of the drawing wherein like reference characters refer to like parts, there is shown in FIG. 1 a schematic illustration of a MR (magnetic resonance) system as is known to those skilled in the art which also generally illustrates the concept of MRI (magnetic resonance imaging). Such an MR system includes a RF (radio frequency) source 2, magnetic field generator(s) 6 (e.g., main and gradient magnetic field generators), a receiver 8, a signal processing mechanism and a display device 16.

The RF source 2 provides pulsed RF energy to the specimen which, in the form shown, is a patient 4 in the main magnetic field which is created by magnetic field generator 6. The RF energy is provided by an RF power amplifier 11, which is in turn fed by an RF transmitter 13, with analog signals converted in digital-to-analog (D/A) converters 14 a from the MRI scanner's main computer 12. The specimen is generally aligned with the main magnetic field and the RF pulses are imposed perpendicular thereto. Where oblique imaging is employed, the angle of impingement of the vector representing the spatial gradient in the magnetic field will be angularly offset relative to the main field. This arrangement results in excitation of the nuclei within the region of interest, which is the area or volume to be imaged, and causes responsive emission of magnetic energy which is picked up by the receiver 8.

The receiver 8 is connected to a detector 200. Detector 200 can be an active internal MRI detector, a catheter antenna, or any other suitable type of detector. Detector 200 can have a voltage induced in it as a result of such responsive emissions of electro-magnetic energy. The signal emerging from the receiver 8 passes through the signal processing mechanism. In the illustrated embodiment, the signal processing mechanisms includes an analog-to-digital (A/D) converter 10 and a computer. The signal emerging from the receiver 8 is typically an analog signal so the A/D converter 10 converts the analog signal to a digital signal for processing within the computer 12.

The computer 12 typically includes one or more applications programs for execution therein, which applications programs typically control image acquisition and signal processing. The applications programs for signal processing can include for example, instructions and criteria for performing FT image construction in one, two or three dimensions, wherein the plot of amplitude versus time corresponding to the incoming signals is converted by FT to a map of the spatial distribution of the signals by plotting amplitude versus frequency or phase in one, two or three dimensions. The FTs are performed in order to establish the MR signal intensity values and the locations of specific pixels. These values may be stored, enhanced or otherwise processed and emerge to be displayed on a suitable screen or display 16. The display can be any of a number of devices or systems known to those skilled in the art, including a cathode-ray tube, a liquid crystal display device, a plasma display device, a light emitting diode (LED) display device, or digital projection device such as that embodying DLP technology, or a printer.

Figure 2:
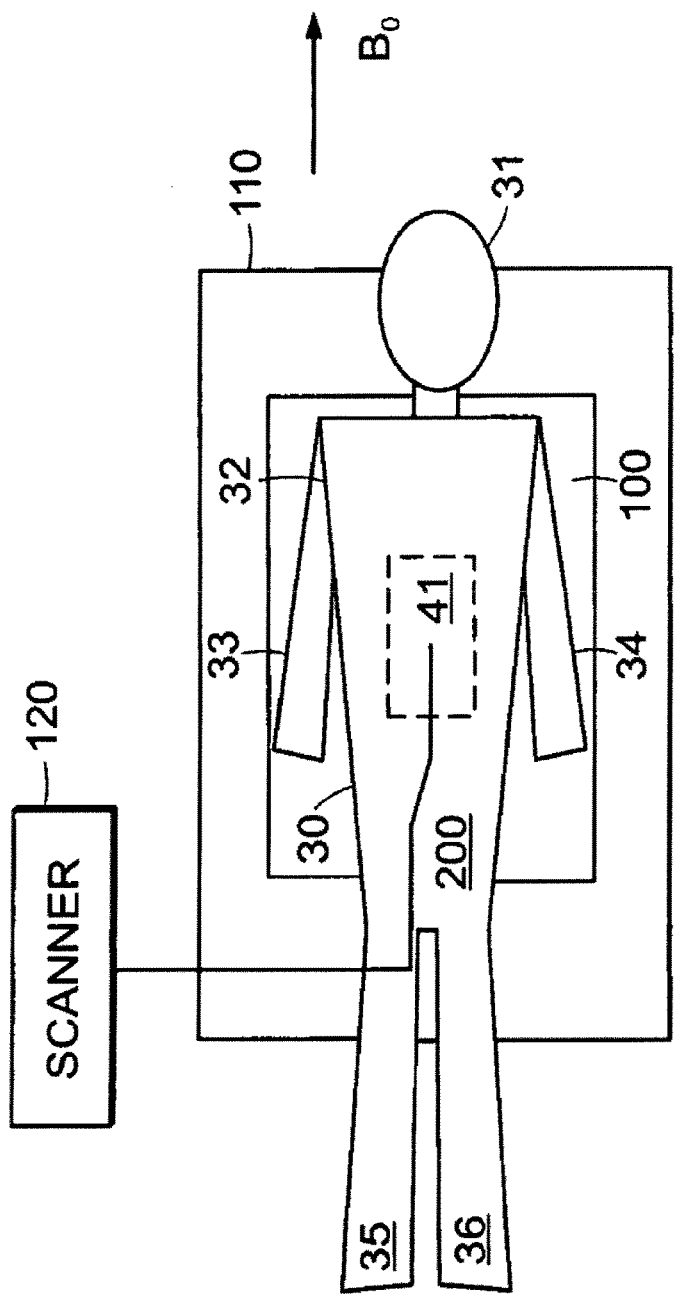
FIG. 2 shows another example embodiment of an MRI system.

As shown in FIG. 2, a specimen 30, which in the illustrated case is a human being, has a head 31, a trunk 32, arms 33, 34, and legs 35, 36. The specimen 30 is disposed adjacent to a body coil 100 within the main magnetic field generated by magnet system 110. The magnet system 110 may be any magnet suitable for use in a MRI scanner, such as a permanent magnet, a superconductor or a resistive magnet, for example, and provided also with gradient magnetic field coils to spatially encode the responsive signals, and may also include RF magnetic coils for exciting the responsive signals, in accordance with the principles of MRI. A detector 200 which may be a loop or a loopless antenna has been introduced into the patient 30 in a conventional manner, for example, through the femoral artery and into the trunk 32 with the antenna being adjacent to the region of interest 41. It should be recognized that this is illustrative and that a detector 200 of the present invention is adaptable so as to be inserted through a naturally existing openings such as a pancreatic duct (e.g., accessible during surgery on the duodenum), bile duct, urethra, urethra, esophagus, the bronchial passages and the like, or a man-made opening such as a catheter sleeve opening in the femoral or other artery, or into the abdomen, or in any other manner consistent with endoscopy, or into tissue via a needle etc.

The detector 200 is operatively associated with a MR scanner 120. The long axis of the detector 200 can be generally aligned with the main magnetic field $B_0$. In this alignment, for example, the sensitivity of the loopless antenna is orthogonal to $B_0$ and is therefore suitable for MR. Similarly, in other embodiments, it should be understood that the alignment of catheter antennae is such that they have a $B_1$ RF field sensitivity to MR signals whose magnetic fields are oriented in planes orthogonal to $B_0$. The detector 200 of the present invention also may be employed with any of a number of encoding methods known to those skilled in the art.

The detector 200 can be moved through orifices, blood vessels or tissues in the body with the intrinsic high-sensitivity to pathology that characterizes MRI. Images constructed using detector 200 can allow users to see through vessel walls, detect plaques etc, at high resolution. See, Qian D, Bottomley P A, "High-resolution intravascular magnetic resonance quantification of atherosclerotic plaque at 3T", Journal of Cardiovascular Magnetic Resonance, 2012: 14:20, doi:10.1186/1532-429X-14-20.

Conventional techniques can allow imaging to proceed at up to approximately 2 frames per second, for example (see, Sathyanarayana S, Schär M, Kraitchman D L, Bottomley P A, "Towards real-time intravascular endoscopic MRI", J Am Coll Cardiol Img 2010; 3: 1158-1165. NIHMSID #251914). This means that probe advancement is limited by the scan time (—0.5 s) if the effect of motion associated with advancement on image quality is to be avoided. Generally, to avoid such "motion artefacts" during that ~0.5 s, a full set of image projections must be acquired before the image can be seen. This is typically 50-256 projections, which would mean that each projection is acquired in about 2-10 ms, equal to the sequence repetition time, TR. Even when the probe is not being advanced motion artefacts may result from physiological or sporadic events that occur during the finite time required for an image acquisition.

Figure 3A:
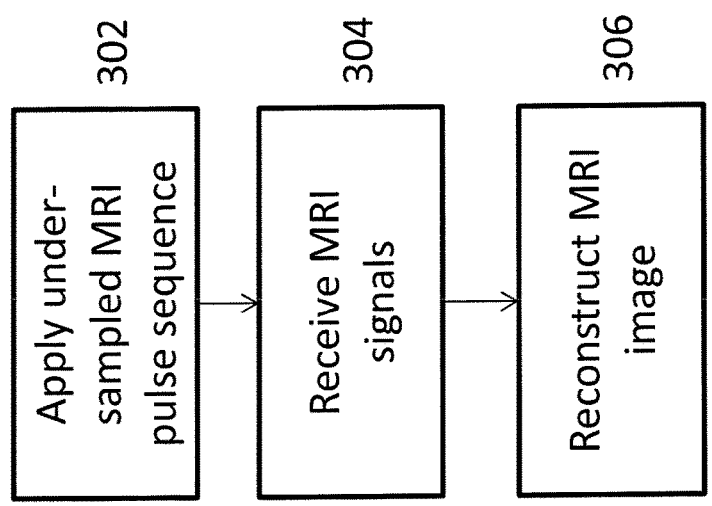
FIGS. 3A-3C shows examples of processes for MRI imaging according to embodiments of the present invention.

FIG. 3A shows an example of a process for increasing this image acquisition speed when performing internal MRI. At step 302, magnet system 110 can apply an MRI pulse sequence to a sample of interest. In some embodiments, the MRI pulse sequence can include spatial encoding projections. In some embodiments, this MRI pulse sequence can be, for example, a projection MRI sequence or a Cartesian MRI sequence.

The sample of interest can include a detector 200, which at step 304 can receive MRI signals caused by the MRI pulse sequence. At step 306, scanner 120, using for example a computer such as computer 12, can reconstruct a magnetic resonance (MR) image or images from the MR signals. Computer 12 can reconstruct these images using, for example an error minimizing algorithm. In some embodiments, the error minimization algorithm can be an iterative error minimization algorithm. In further embodiments, the error minimization algorithm can be an $l_1$-norm minimization algorithm, and images can be reconstructed using a Wavelet Transform The MRI pulse sequence used in the process of FIG. 3 can provide an increase in an acquisition speed when reconstructing the MR image or images by sparsely undersampling an image k-space in at least one dimension. This increase in acquisition speed can be proportionate to an undersampling factor of the MRI pulse sequence, which can be a measure of the amount of undersampling conducted when compared to a fully-sampled pulse sequence. In some embodiments, a projection MRI sequence can be randomly undersampled. In further embodiments, the MRI pulse sequence can be a Cartesian MRI sequence with a variable-density random under-sampled Cartesian MRI sequence with minimum undersampling at the center of k-space.

In some embodiments, the MRI pulse sequence can be applied repeatedly and the reconstructed MRI image or images can be part of a cine stream. This cine stream can be created by successively replacing the oldest acquired of said spatially-encoding projection of the MRI sequence, with the most recently acquired spatially-encoding projection.

High-resolution intravascular (IV) MRI is susceptible to degradation from physiological motion, and requires high frame-rates for true endoscopy. Fortunately, IV MRI detectors, for example detector 200, can have intrinsically radial and sparsely-localized sensitivity profiles, and high local signal-to-noise ratios (SNR). Some embodiments of the current invention can combine compressed sensing with sparse reconstruction and motion correction using frame-by-frame projection shifting that is based on a singularity at the probe's location to provide a many-fold effective speed-up in image acquisition as well as a significant reduction in motion sensitivity. In some examples according to embodiments of the current invention, we present data acquired in phantoms, and human vessel specimens. These strategies can greatly facilitate high-resolution (~100 μm) real-time internal MRI and/or MRI endoscopy.

Under-sampling schemes are being applied to dramatically speed up conventional MRI for real-time imaging applications where dynamic response or motion-suppression is key, including the heart and functional MRI (fMRI), but not intra-vascular (IV) or internal MRI. As first demonstrated here, internal MRI and/or MRI endoscopy with its very high local SNR, intrinsically localized/sparse characteristics, and need for speed, can be a candidate for these techniques. Accordingly, some embodiments of the current invention provide under-sampling methods for MRI, which can provide a significant speed-up in scan time (examples here are up to 4-fold).

The technique can be combined with the method of reducing motion sensitivity, described in U.S. App. No. 61/703,674 "Motion-insensitive, projection-based MRI endoscopy method", filed Sep. 20, 2012, the entire contents of which are hereby incorporated herein by reference. That method takes advantage of the intrinsic radial symmetry of internal detectors, replacing inter-scan image-shifting of the original internal MRI method, with intra-scan projection shifting. This not only fixes the endoscope's viewpoint to the center of the image FOV in real time, but also enables "sliding window" acquisitions wherein the oldest projections are replaced with the newest projections, since all the projections will be co-registered. Combining the two methods involves replacing the conventional set of MRI projections, with an under-sampled set of projections and employing sparse reconstruction methods.

Figure 3B:
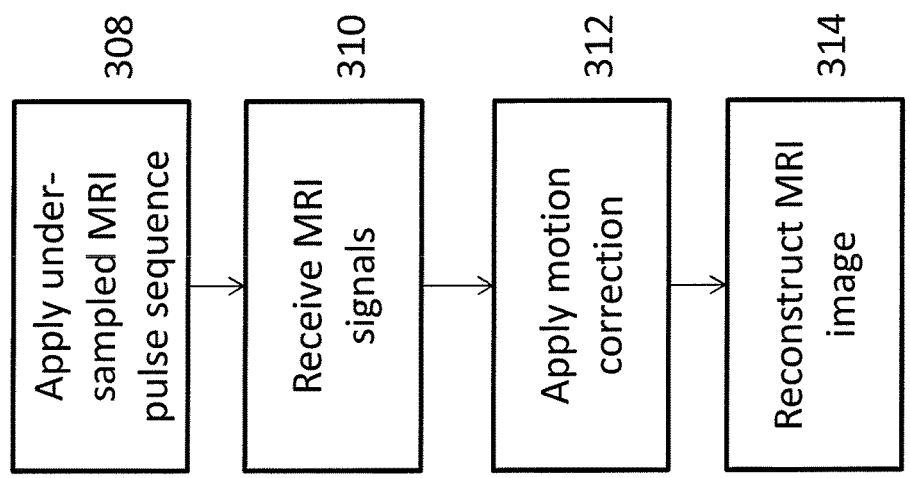

Referring back FIG. 3B, at step 308, an undersampled pulse sequence can be applied to a region of interest, and at step 310 a detector can be located within that region of interest, for example detector 200. At step 312 this motion correction can be applied, and at step 314 MR image or images can be reconstructed, using for example an error minimizing algorithm. In this motion correction technique, every projection frame can be motion-corrected before it is fed to the image reconstruction. In addition, switching to the projection reconstruction method, means that every frame in the image sequence can be a projection. See, Lauterbur P C., "Image Formation by Induced Local Interactions: Examples Employing Nuclear Magnetic Resonance"; Nature, 1973; 242: 190-191.

This motion correction can include reconstructing the MR image or images from a viewpoint of detector 200 at a center of a MRI field of view. In at least one spatially-encoding projection excited by an MRI pulse sequence, an MRI signal of detector 200 can exhibit at least one singularity in a vicinity of a location of detector 200. A location of the singularity can be detected in the at least one projection using a detection algorithm, and the projection can be shifted to the center of the MRI field of view prior to image reconstruction. In other embodiments, one or more of the projections which are determined to be corrupted by motion can be discarded, and another projection, for example a projection with the same encoding, can be acquired as a replacement.

The singularity can be defined as one or more points in the projection where a sensitivity of the detector 200 undergoes a transition from substantially an MRI signal maximum immediately adjacent to detector 200 to substantially a signal void at the location of the detector 200. In other embodiments, a singularity can be defined as one or more points in the projection where a phase of the detector 200 undergoes a substantial reversal from at least at one location adjacent to detector 200 as compared to a location diametrically opposite the at least one adjacent location. The detection algorithm can be a cross-correlation algorithm or a maximum gradient detection algorithm applied to either the sensitivity singularity or the phase singularity, or to a combination of both sensitivity and phase singularities Using this motion correction, the MRI system can generate under-sampling MRI pulse sequence creating a stream of spatially-encoding projections wherein singularities are detected, and can shift each projection to the center of the FOV thereby creating a set of spatially shifted projections, and then at step 314 reconstruct at least one image from said set of projections.

FIG. 12(a) illustrates an image of a probe which can make use of this motion correction technique, which can be, for example, detector 200. Since internal coils are embedded in the body, any motion of the subject can cause coil motion. The sensitivity profile of the probes allows coil detection in individual radial projections. Hence, each can be individually shifted to reduce or track motion.

In addition, it is noted that the RF field strength and sensitivity of internal probes fall drastically with distance r away from the probe. FIG. 12(b) illustrates the axial field of a loopless antenna. Also, the detection phase varies azimuthally around the probe. So, for each projection, we can almost invariably observe an amplitude crater at the probe, as shown in FIG. 12(c), and a phase reversal at the probe, as shown in FIG. 12(d).

This motion correction technique can be used in conjunction with an MRI scanner such as detailed and embodied in U.S. Pat. No. 4,689,563, which is incorporated by reference herein, modified with the additional features of the present invention, in conjunction with an internal MRI endoscope is what is envisaged, preferably operating at an MRI field strength between 1.0 and 7.0 Tesla.

This motion correction technique can also be used in conjunction with the systems described in U.S. Patent Publication No. 2010/0256480, U.S. Pat. Nos. 5,699,801, and 5,928,145, each of the references being incorporated by reference herein. See also, Ocali O, Atalar E, "Intravascular magnetic resonance imaging using a loopless catheter antenna", Magn. Reson/ Med. 1997; 37:112-118, which is also incorporated by reference herein.

Figure 3C:
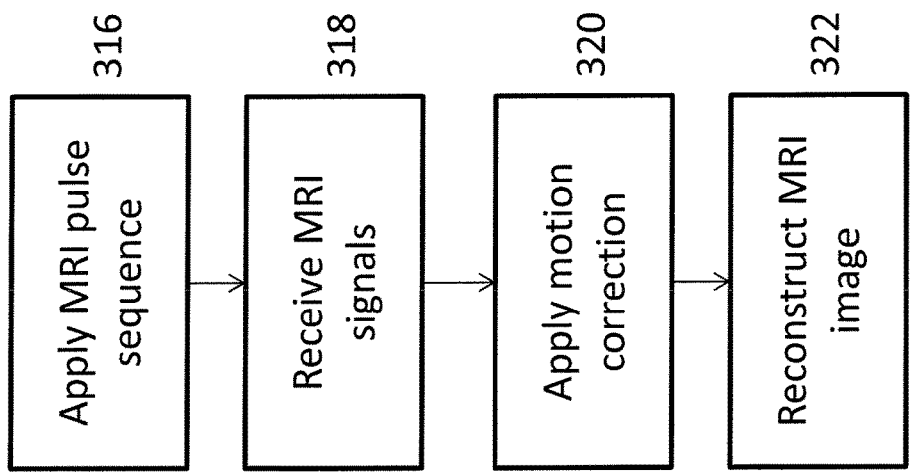

In some embodiments, this motion correction technique can also be used without an undersampled pulse sequence. FIG. 3C shows an example process for motion correction when performing internal MRI. At step 316, a pulse sequence can be applied to a region of interest, and at step 318 a detector can be located within that region of interest, for example detector 200. At step 320 this motion correction can be applied, as discussed above, and at step 322 MR image or images can be reconstructed, using for example an error minimizing algorithm.

Implementing this technology in real-time can both speed-up and reduce artifacts from physiologic motion and probe advancement. The advances could play an enabling role for internal MRI and MRI endoscopy.

As noted above, current speeds for intravascular (IV) MRI and MRI endoscopy[1] are limited to ~2 frames/s at 3 T, rendering high-resolution (~100 μm) images susceptible to degradation by physiological and random motions with amplitudes and periods of the order of mm/ms. Accordingly, some embodiments of the current invention use projection reconstruction MRI as follows:

(A) reduce sensitivity to motion from the time-scale of individual images, to the time-frame of each projection (TR) by frame-shifting each projection to the center of the FOV defined by the location of the antenna, prior to reconstruction; and/or (B) apply compressed sensing to provide acceleration factors of several- or many-fold.

In the examples, we present data acquired in phantoms (fruit), human vessel specimens and/or apply the methods to retro-actively acquired data with speed-up factors of up to 4-fold.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The following Examples are offered by way of illustration and not by way of limitation.

(A) Motion correction. IV MRI with and without mechanical motion, was performed on a Philips 3 T MRI scanner using a 2 mm diameter 3 T loopless antenna receiver, and a radial k-space traversal. As shown in FIGS. 4A-4F, we note that in each projection:

(i) there is intense signal surrounding the probe, but the probe itself produces no signal. The amplitude peaks with two gradient reversals adjacent to a nadir at the probe wire (FIGS. 4A and 4B).

Figures 4A, 4B, 4C, 4D, 4E, 4F:
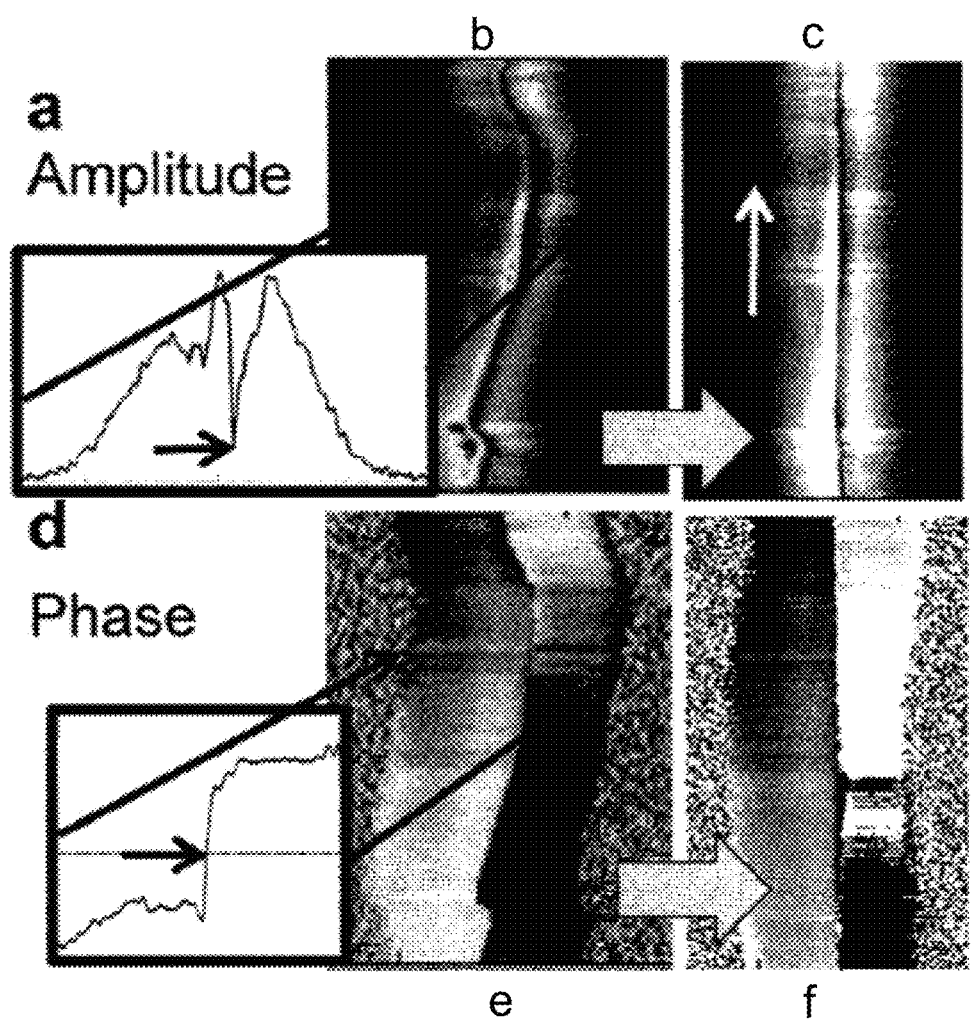
FIGS. 4A-4F show, respectively, signal amplitude (a-c, FIGS. 4A-4C) and phase (d-f, FIGS. 4D-4F) of MRI endoscope and show singularities (thin arrows), signal amplitude and phase track with motion (b,e, FIG. 4B and FIG. 4E) and signal amplitude and phase are used to translate projection to the center of the image field-of-view (FOV) (c,f, FIG. 4C and FIG. 4F).

(ii) Further, there is a phase reversal that occurs at the probe (FIG. 4*d*).

(iii) these two signal 'singularities' aren't always at the exact center of the projection, and their location may vary with time in the presence of motion (FIG. 4B, 4E).

The method according to an embodiment of the current invention involves detection of the amplitude and phase singularities at the probe's location using a signal derivative algorithm or a cross-correlation algorithm. After detection of the singularity, the entire projection is shifted to the center of the field-of-view (FOV). This is repeated for successive projections, so that all projections are aligned with respect to the location of the projection (FIG. 4C, 4F). Images reconstructed from these re-aligned projections always have the probe at the center of the FOV.

Figures 5A, 5B, 5C:
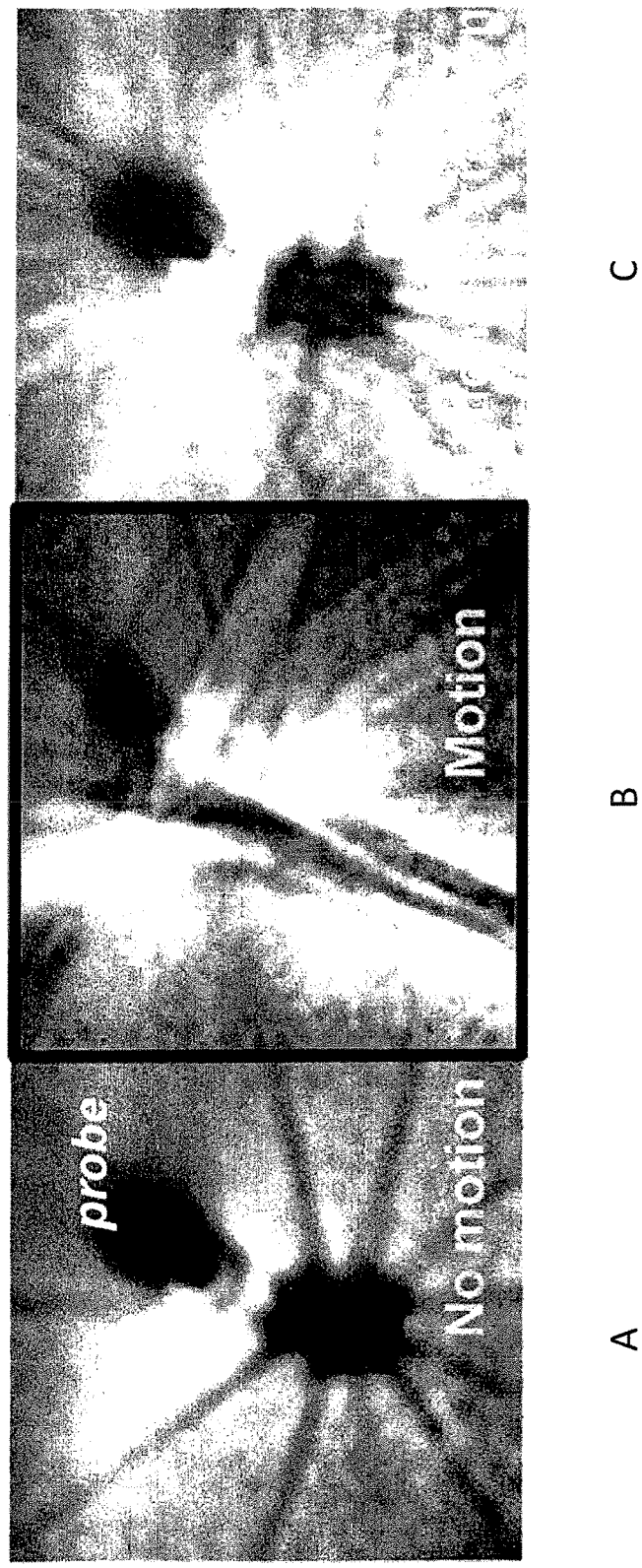
FIGS. 5A-5C show corrective effect of projection shifting on severe motion of an endoscope in an orange.
Figures 14A, 14B, 14C, 14D, 14E:
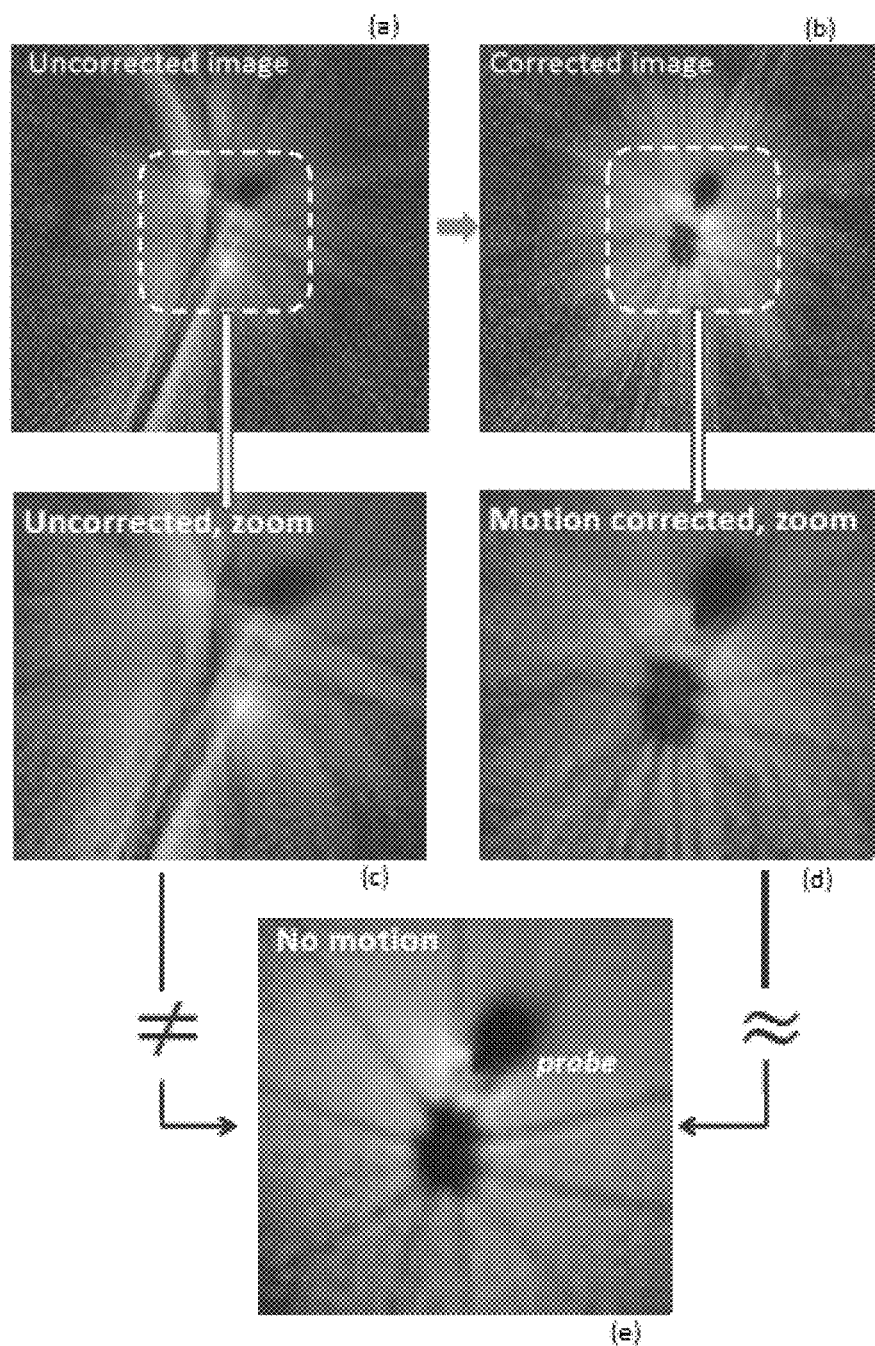
FIG. 14A shows an uncorrected image according to features of the present invention.
FIG. 14B shows a corrected image using image filter according to features of the present invention.
FIG. 14C shows an uncorrected image in zoom according to features of the present invention.
FIG. 14D shows a corrected motion image in zoom using image filter according to features of the present invention.
FIG. 14E shows no motion of the probe.

Results from a loopless antenna MRI detector inserted into an orange (FIG. 5A, at rest) show severe motion artefacts when the orange is manually shaken (+/−3 mm) in a 3 T scanner while imaging using a loopless antenna (FIGS. 5B, 14A). Two-hundred projections spanning the entire circle were obtained in each case of the orange at rest and in motion. To obtain FIGS. 5C, 14B, the probe location was detected and each projection aligned with the probe as center in accordance with an embodiment of the invention, followed by image reconstruction performed by filtered-back projection of the aligned projections. As is evident, the motion artefact is greatly reduced by applying the correction to the same data set, according to an embodiment of the current invention, as compared to the uncorrected image (FIGS. 5C vs 5B).

(B) Compressed sensing is a method wherein a number of frames of the image k-space are omitted during image acquisition permitting a sharp reduction in scan time[2-7]. The resultant "sparsely sampled" image is usually reconstructed with wavelet transform (WT) techniques, that can produce speed-up factors of 3-4-fold or potentially more. The image reconstruction—often with little loss in image quality—can use an iterative error minimization algorithm such as the so-called "$l_1$-norm" minimization. The utility of the WT, which underlies compression methods including JPEG, lies in its ability to transform image content into a vector of sparse components that permits encoding with just a few significant coefficients. For MRI, only the limited subset of image k-space acquisitions that correspond to this sparsely sampled data set need be directly measured, reducing the scan-time proportionately[3].

Compressed sensing has been previously proposed and implemented to speed up conventional MRI and angiography. It is also used in other image applications involving data and image compression. It has not, however, been used for MRI endoscopy with either radial projection or Cartesian MRI pulse sequences, nor in conjunction with internal MRI detectors. Nevertheless, it is well-suited to be adapted for these applications because the endoscopic MRI signal is highly localized to regions close to the probe (FIGS. 4, 5), and wherein regions far from the probe in image space possess little or no signal. For radial projection imaging, the data set is "sparsified" by means of random or uniform under-sampling[2]. Variable-density random under-sampling may be used on MRI data acquired from Cartesian data sets, retaining most of the frames close to the center of image k-space[2-3] in accordance with an embodiment of the present invention. The images are reconstructed using "$l_1$-norm" minimization and WT.

The sparse sampling method is based on information theory where it has been shown that an unknown signal can be reconstructed with a sampling rate significantly below the Nyquist frequency, if the underlying unknown signal is sparse or can be sparsified in some transform domain. According to compressed sensing theory, in order to reconstruct an MRI image, ρ, from an undersampled Fourier encoded signal, $s_u$, it should satisfy[3]:

$$\min_{\rho}\|\psi\rho\|_1 \text{ subject to } \|F_u\rho - s_u\|_2 \le \varepsilon, \quad (1)$$

where $\psi$ is a sparsifying transform matrix, such as wavelet or random sensing matrix[10]; $\|\cdot\|_1$ is $l_1$-norm defined as $$\|x\|_1 = \sum_i |x_i|; \|\cdot\|_2$$

is $l_2$-norm defined as $$\|x\|_2 = \sqrt{\sum_i |x_i|^2};$$

$F_u$ is the undersampled Fourier encoding operator; and $\varepsilon$ accounts for reconstruction error including noise.

Figures 6A, 6B, 6C:
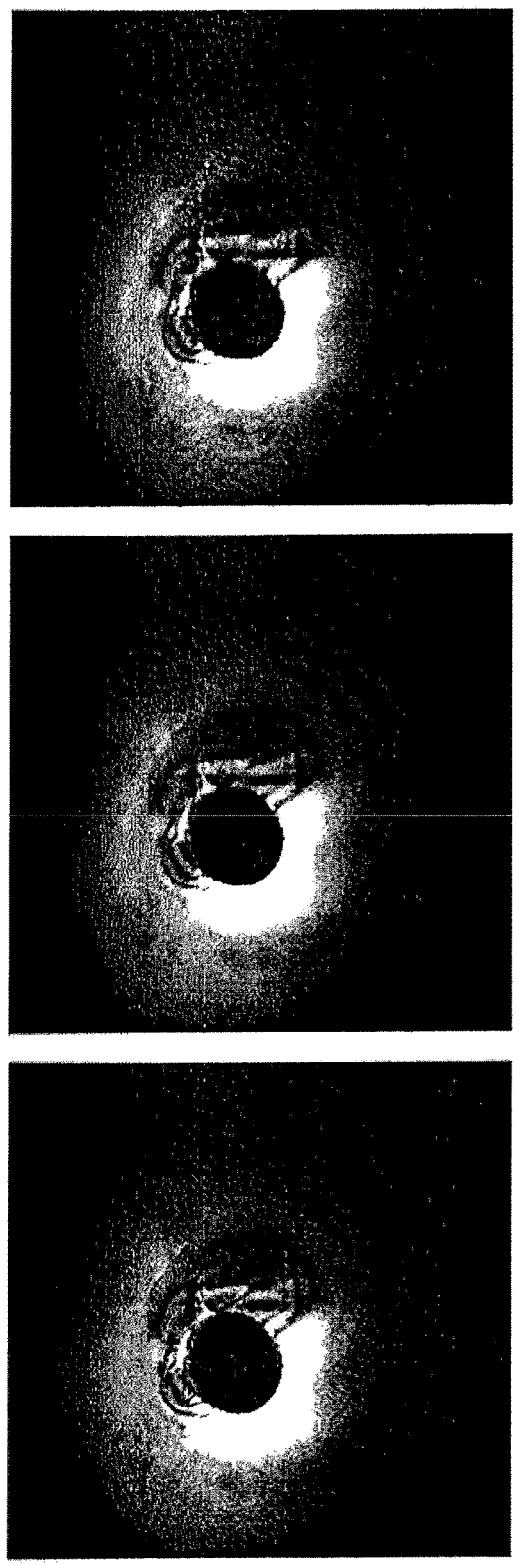
FIGS. 6A-6C show, respectively, (a, FIG. 6A) original image from fully sampled image k-space; (b, FIG.6B) Compressed sensing reconstruction from ~⅓ of k-space data, and (c, FIG. 6C) Fourier reconstruction from same k-space data as (b, FIG. 6B) and with missing lines zero filled.

For numeric minimization and reconstruction, Eq. (1) is formulated as a weighted objective function:

$$\min_{\rho}\{\|F_u\rho - s_u\|_2 + \lambda_1\|\psi\rho\|_1 + \lambda_2 \nabla \rho\}, \quad (2)$$

where $\lambda_1$ and $\lambda_2$ are regularization parameters; and $\nabla\rho$ is the finite difference or total variation[11]. The first term in Eq. (2) ensures that the result is consistent with the acquired signal. The second $l_1$-norm term promotes sparseness in the $\psi$-transformed domain, and the total variation term preserves image gradients or edge information. Numeric optimization of Eq. (2) yields the unknown image, $\rho$ which is largely free of Nyquist aliasing artifacts, as shown in FIGS. 6A-6C.

Figures 7A, 7B, 7C:
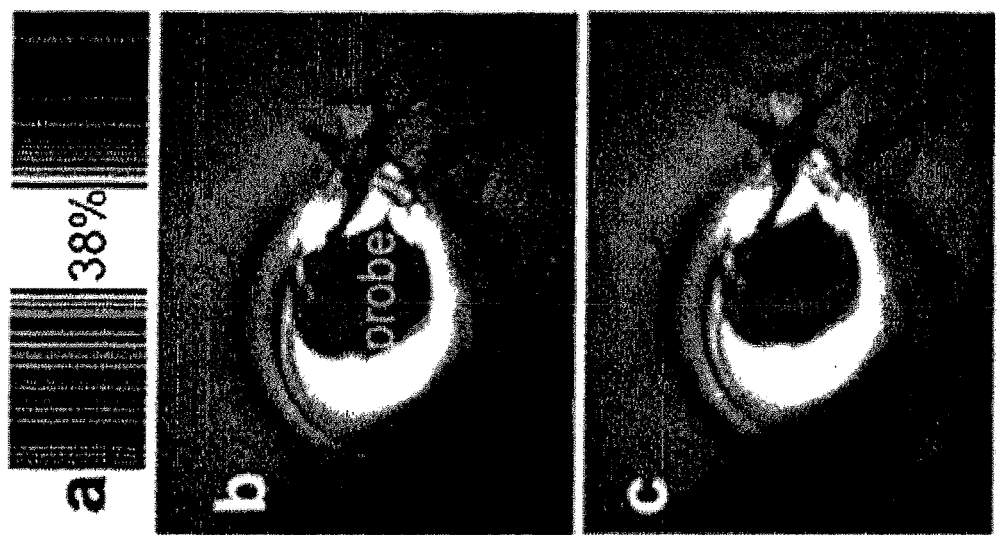
FIG. 7A-7C show, respectively, (a, FIG. 7A) Under-sampling pattern applied to 80 μm in vivo endoscopic MRI from rabbit aorta; (b, FIG. 7B) 80 μm in vivo endoscopic MRI from rabbit aorta to obtain sparse image from 38% of the same data; and (c, FIG. 7C) the sparse image from 38% of the same data.

Sparsely under-sampled reconstruction was tested with Cartesian MRI endoscopy data acquired from a rabbit in vivo in a 3 Tesla clinical research MRI scanner with 80 µm resolution (8 slices, 5 min, ~38 s/slice[1]. Applying the (38%) variable density random under-sampling pattern shown in FIG. 7A to the phase-encoding ($k_y$) MRI steps, yields, after reconstruction to minimize the "$l_1$-norm" of the WT-transformed images[3], results that are virtually equivalent to the original image (FIG. 7B vs. 7C), effectively 2.5-times faster—about 15 s for this 80 µm resolution image.

Figure 8B:
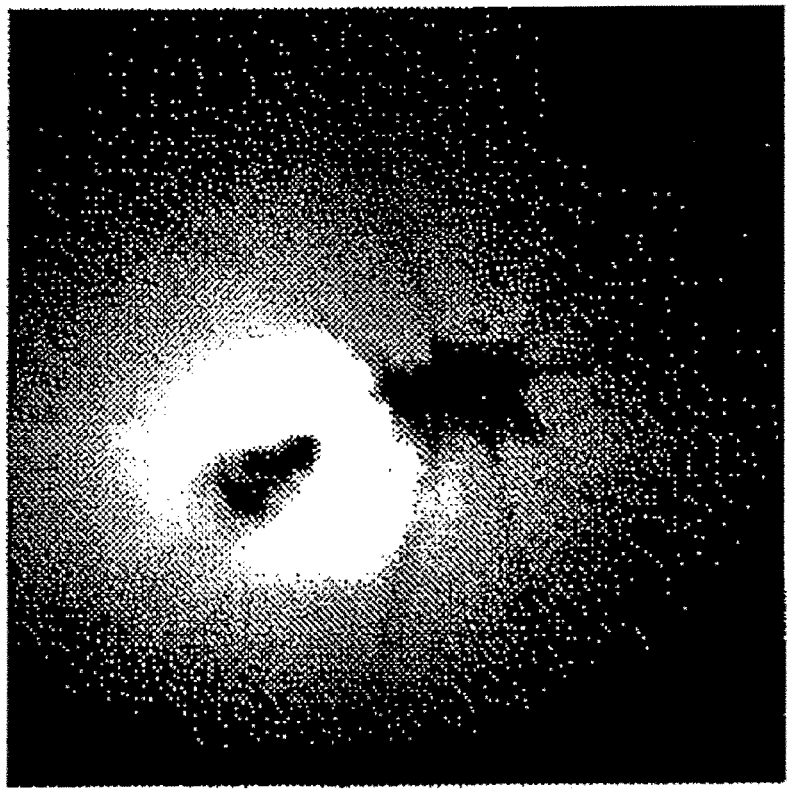
FIGS. 8A-8B show radial projection internal MRI in an orange; (a, FIG. 8A) Conventional image; and (b, FIG. 8B) 25%-undersampled/sparse.
Figure 8A:
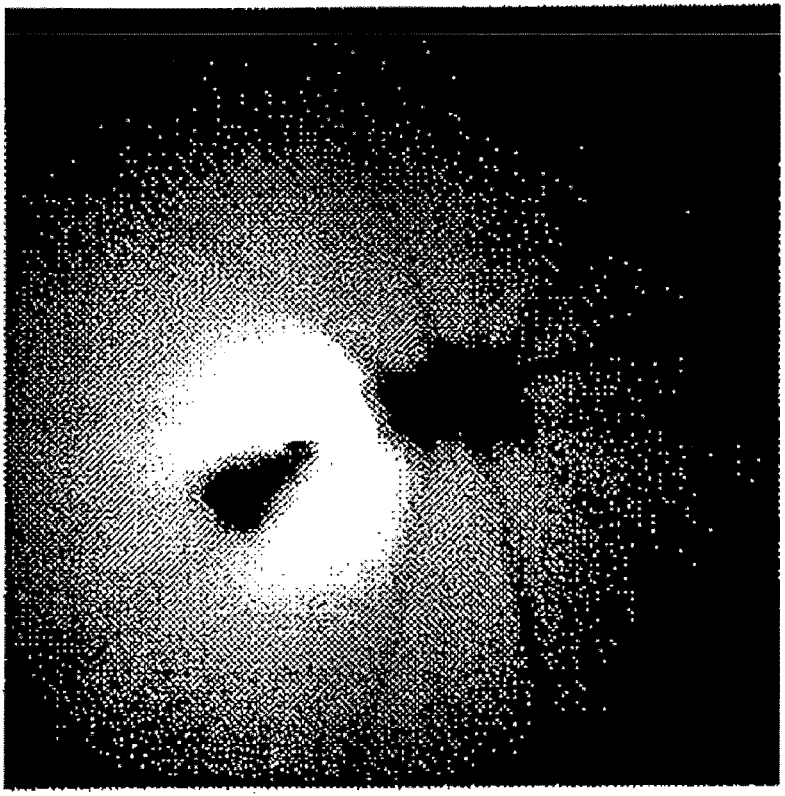
Figures 9A, 9B, 9C, 9D, 9E, 9F:
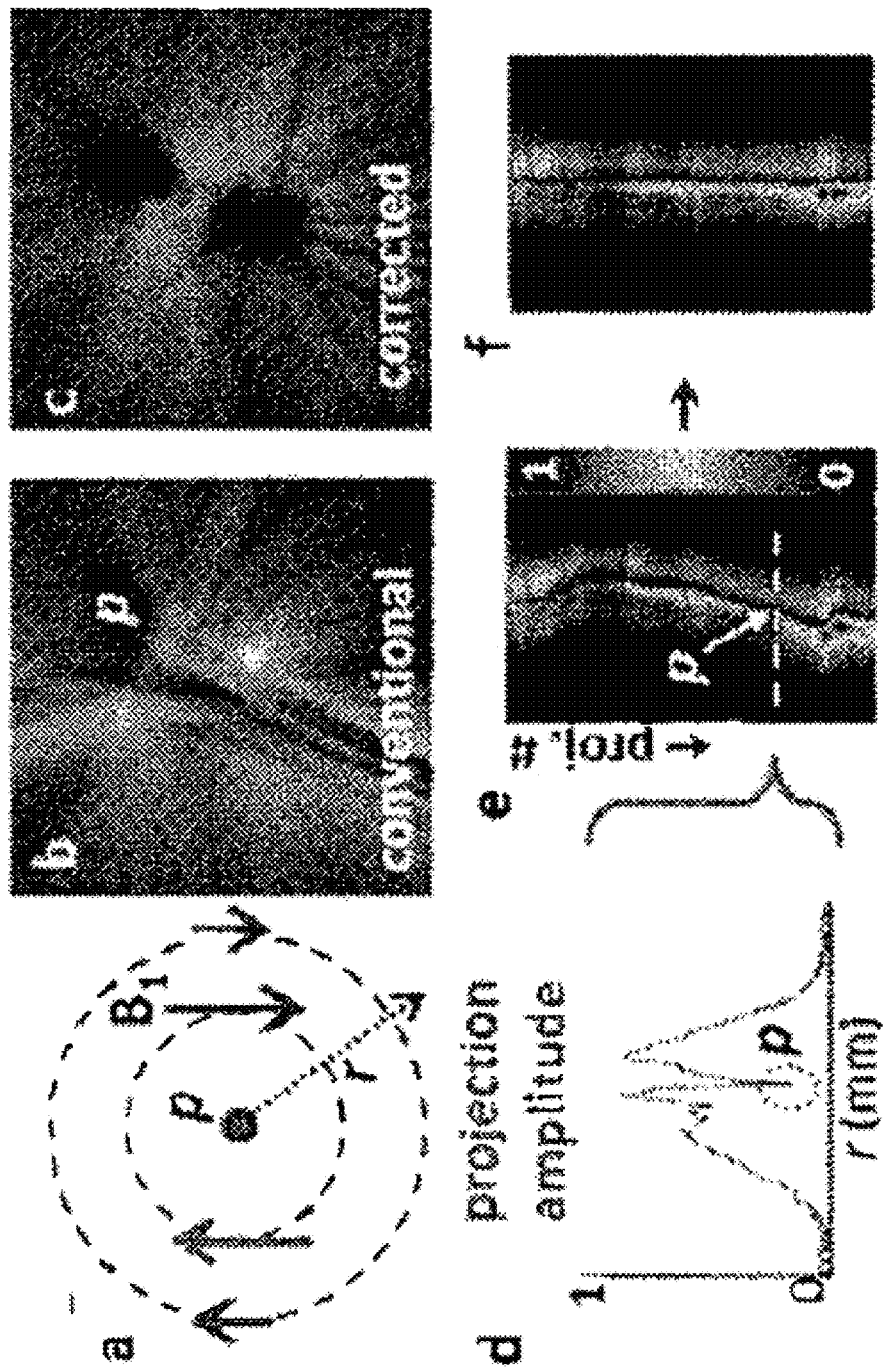
FIGS. 9A-9F show, respectively, (a, FIG. 9A) an example of a transverse field of a loopless antenna detector p shows decreasing $B_1$ with r and azimuthal variation in phase; (b, FIG. 9B) MRI of an orange shaken ±3 mm (20 radial GRE; 200 spokes spanning 180°; 250 gm in-plane resolution; TR/TE=15/6 ms) shows debilitating motion artifacts; (c, FIG.9C) Projection shifting all but removes streaking, revealing the fruit's underlying structure; (d-f, FIG. 9D-FIG. 9F) an example of a motion correction algorithm re-aligns every azimuthal projection on p.
Figures 10A, 10B:
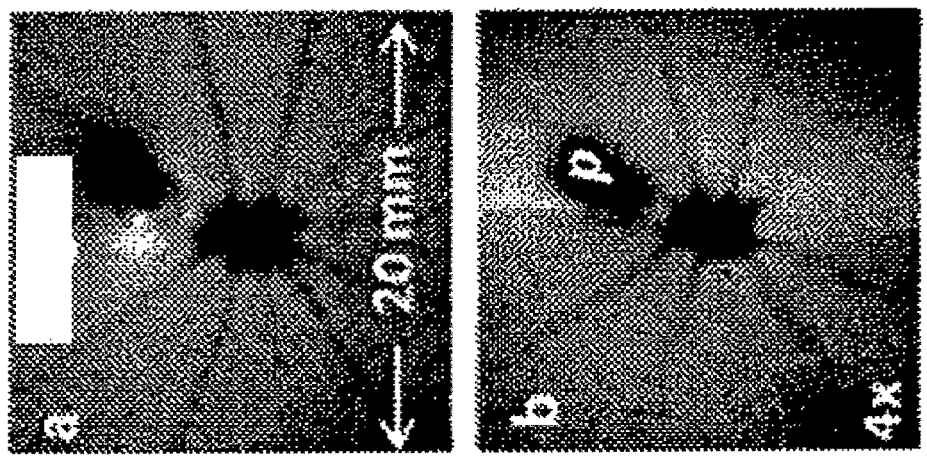
FIGS. 10A-10B show, respectively, fruit morphology using the complete data set (a, FIG. 10A), the fruit morphology is retained in a four-fold under-sampled radial-compressed sense reconstruction (b, FIG. 10B).
Figures 11A, 11B:
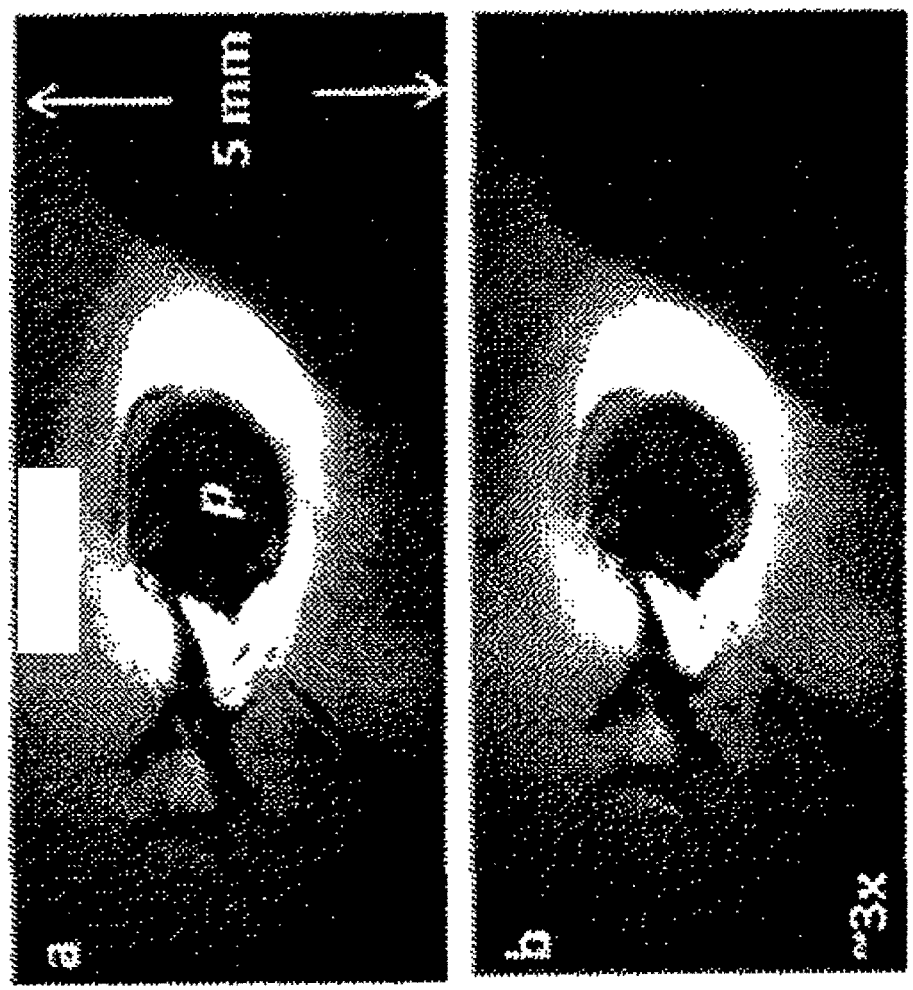
FIGS. 11A-11B show, respectively, (a, FIG. 11A) Regular Cartesian MRI endoscopy of a rabbit aorta in vivo (3D GRE; TR/TE=250/12 ms; in-plane resolution 8011 m; 3.1 min/5 contiguous slices); and (b, FIG. 11B) threefold under-sampling yields a virtually indistinguishable image (cropped for visualization) after compressed-sense reconstruction.

With radial projections, k-space is sampled randomly or uniformly (exemplified in FIG. 8). In another experiment on an orange, we cut the original data set to 25%, and used an $l_1$-norm minimization of the total variation of pixel signals to produce a radial projection image effectively 4-times faster (see FIG. 8B vs 8A). Radial and Cartesian compressed sensing produced virtually indistinguishable images with only $\frac{1}{4}^{th}$ to $\frac{1}{3}^{rd}$ of the original data.

Since the motion correction algorithm acts on each projection, it was also applied to a radially under-sampled data set (not shown).

These novel techniques can take advantage of the intrinsic radial symmetry of these detectors. By replacing inter-scan image-shifting of prior methods including MRI endoscopy[1], with intra-scan projection shifting, not only fixes the internal antenna's viewpoint to the FOV center in real time, but also enable "sliding window" acquisitions replacing the oldest with the newest projections, since all the projections are already co-registered. Thus, implementing the motion correction method in real-time can significantly reduce artifacts from physiologic motion and probe advancement. Undersampling can dramatically speed-up conventional MRI for applications where dynamic response or motion-suppression is key, as first demonstrated here for internal MRI, with high local SNR, intrinsically localized/sparse characteristics, and need for speed, make it an ideal application.

As a result, intra-vascular (IV), intra-orifice, and/or needle-mounted MRI detectors operating in human scanners operating at, for example at 1-7 Tesla, can be well-suited to compressed sensing and motion correction strategies based on their intrinsically radial and sparsely-localized sensitivity profiles and high signal-to-noise ratios. The benefits can include much faster IV MRI-approaching real-time (~10 fr/s) and reduced motion sensitivity, while retaining the high-resolution (80-300 µm) image information.

Figures 13A, 13B, 13C, 13D:
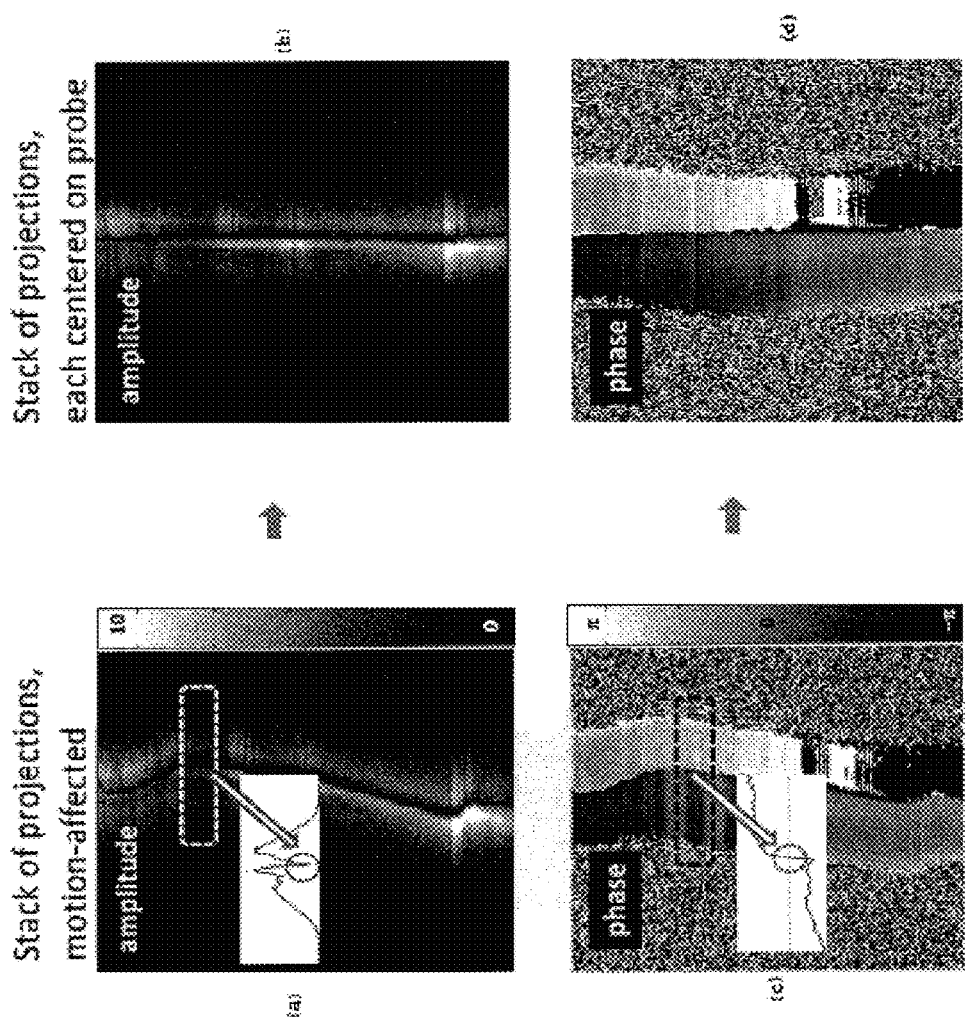
FIG. 13A shows a stack of projections, motion affected, by amplitude according to the features of the present invention.
FIG. 13B shows a stack of projections, each centered on probe, by amplitude according to the features of the present invention.
FIG. 13C shows a stack of projections, motion affected, by phase according to the features of the present invention.
FIG. 13D shows a stack of projections, each centered on probe, by phase according to the features of the present invention.

FIGS. 13 and 14 further illustrate the example of motion correction in corresponding to FIGS. 4 and 5. An orange was manually shaken (+/−3 mm) in a 3T scanner while imaging using a loopless antenna. Two-hundred projections spanning the entire circle were obtained. Each projection was aligned with the probe as center. Image reconstruction was performed by filtered-back projection of aligned projections. FIG. 13 (a) illustrates a stack of projections, motion affected, by amplitude according to the features of the present invention. FIG. 13 (b) illustrates a stack of projections, each centered on probe, by amplitude according to the features of the present invention. FIG. 13 (c) illustrates a stack of projections, motion affected, by phase according to the features of the present invention. FIG. 13 (d) illustrates a stack of projections, each centered on probe, by phase according to the features of the present invention.

Both the amplitude- and phase-based methods produced superior images compared to conventional scanner reconstruction. However, some radial streaking remained in the fringe field of view when compared to a no-motion image, which could be remedied by removing and re-aquiring aberrant projections. FIGS. 14(a)-(e) compare the results.

In particular, FIG. 14 (a) illustrates an uncorrected image according to features of the present invention. FIG. 14(b) illustrates a corrected image using image filter according to features of the present invention. FIG. 14(c) illustrates an uncorrected image in zoom according to features of the present invention. FIG. 14(d) illustrates a corrected motion image in zoom using image filter according to features of the present invention. FIG. 14(e) illustrates no motion of the probe.

REFERENCES

1. Sathyanarayana S, et. al., JACC Cardiovasc Imaging. 2010; 3(11):1158-1165.
2. Block et. al, Magn Reson Med 2007; 57: 1086-1098.
3. Lustig et. al, Magn Reson Med, 2007; 58(6):1182-1195.
4. Jung H, Ye J C, Kim E Y. Improved k-t BLASK and k-t SENSE using FOCUSS. Phys Med Biol 2007; 52: 3201-3226.
5. Gamper U, Boesiger P, Kozerke S. Compressed sensing in dynamic MRI. Magn Reson Med 2008; 59: 365-373.
6. Jung H, Park J, Yoo J, Ye C. Radial k-t FOCUSS for High-Resolution Cardiac Cine MRI. Magn Reson Med 2010; 63:68-78.
7. Usman M, Atkinson D, Odille F, Kolbitsc C, Vaillant G, Schaeffter T, Batchelor P G, Prieto C. Motion Corrected Compressed Sensing for Free-Breathing Dynamic Cardiac MRI. Magn Reson Med (in press: August 2012: DOI: 10.1002/mrm.24463).

8. Candès E J, Romberg J, Tao T. Robust uncertainty principles: Exact signal reconstruction from highly incomplete frequency information. IEEE Trans Inf Theor 2006; 52: 489-509.
9. Donoho D L. Compressed sensing. IEEE Trans Inf Theor. 2006; 52:1289-1306.
10. Candès E J, Wakin M B. An introduction to compressive sampling. Signal Processing Magazine, IEEE, 25 (2008) 21-30.
11. Rudin L I, Osher S, Fatemi E. Nonlinear total variation based noise removal algorithms. Physica D: Nonlinear Phenomena 1992; 60: 259-268.
12. Hegde S S, Zhang Y, Bottomley P A. Accelerated, motion-corrected high-resolution intravascular MRI at 3T. Proc ISMRM 2013 (In press, April 2013).

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A method of internal MRI comprising:
employing a single active internal MRI detector located within a sample of interest;
applying an MRI pulse sequence to said sample of interest which includes said single active internal MRI detector, said MRI pulse sequence comprising spatial encoding projections;
receiving MRI signals at the single active internal MRI detector; and
reconstructing at least one MRI image from the MRI signals using an error minimizing algorithm, said error minimizing algorithm being a compressed sensing error minimization algorithm,
wherein said MRI pulse sequence provides an increase in an acquisition speed when reconstructing said at least one MRI image by sparsely under-sampling an image k-space in at least one dimension.

2. The method of claim 1, wherein the increase in acquisition speed is proportionate to an undersampling factor of the MRI pulse sequence.

3. The method of claim 1, wherein the MRI pulse sequence is one of a projection MRI sequence or a Cartesian MRI sequence.

4. The method of claim 3, wherein the projection MRI sequence is randomly undersampled, and wherein the Cartesian MRI sequence is a variable-density random undersampled Cartesian MRI sequence with minimum undersampling at the center of k-space.

5. The method of claim 1, wherein the error minimization algorithm is an iterative error minimization algorithm.

6. The method of claim 5, wherein the error minimization algorithm is an $l_1$-norm minimization algorithm, and wherein images are reconstructed using a Wavelet Transform.

7. The method of claim 1, wherein the MRI pulse sequence is applied repeatedly and wherein the reconstructed image is part of a cine stream.

8. The method of claim 7, wherein said cine stream is created by successively replacing the oldest acquired of said spatially-encoding projection of the MRI sequence, with the most recently acquired spatially-encoding projection.

9. A method of internal MRI employing at least one active internal MRI detector located within a sample of interest, comprising:
applying an MRI pulse sequence to said sample of interest which includes said at least one active internal MRI detector, said MRI pulse sequence comprising spatial encoding projections;
receiving MRI signals at the at least one active internal MRI detector;
reconstructing at least one MRI image from the MRI signals using an error minimizing algorithm; and
performing motion correction to said at least one MRI image,
wherein said MRI pulse sequence provides an increase in an acquisition speed when reconstructing said at least one MRI image by sparsely under-sampling an image k-space in at least one dimension,
wherein performing motion correction comprises reconstructing said MRI image from a viewpoint of said at least one active internal MRI detector at a center of a MRI field of view,
wherein, in at least one spatially-encoding projection excited by said MRI pulse sequence, an MRI signal of said detector exhibits at least one singularity in a vicinity of a location of said at least one active internal MRI detector,
wherein a location of the singularity is detected in said at least one projection using a detection algorithm, and
wherein the projection is shifted to the center of the MRI field of view prior to image reconstruction.

10. A method of internal MRI employing at least one active internal MRI detector located within a sample of interest, comprising:
applying an MRI pulse sequence to said sample of interest which includes said at least one active internal MRI detector, said MRI pulse sequence comprising spatial encoding projections;
receiving MRI signals at the at least one active internal MRI detector;
reconstructing at least one MRI image from the MRI signals using an error minimizing algorithm,
wherein said MRI pulse sequence provides an increase in an acquisition speed when reconstructing said at least one MRI image by sparsely under-sampling an image k-space in at least one dimension,
wherein the at least one singularity is defined as one or more points in the projection where one of a sensitivity of the detector undergoes a transition from substantially an MRI signal maximum immediately adjacent to said MRI detector to substantially a signal void at the location of the detector, or a phase of the detector undergoes a substantial reversal from at least at one location adjacent to said MRI detector as compared to a location diametrically opposite to said at least one adjacent location.

11. The method of claim 10, wherein said under-sampling MRI pulse sequence generates a stream of spatially-encoding projections wherein singularities are detected,
wherein each projection is shifted to the center of the field of view thereby creating a set of such spatially shifted projections, and
wherein at least one image is reconstructed from said set of projections.

12. The method of claim 11, wherein the MRI pulse sequence is applied repeatedly and multiple images reconstructed to form a cine stream with said detector always positioned substantially at the center of the image field of view.

13. The method of claim 12, wherein said cine stream is created by successively replacing the oldest acquired of said spatially-encoding projection of the MRI sequence with the most recently acquired spatially-encoding projection.

14. The method of claim 10, wherein said detection algorithm is at least one of a cross-correlation algorithm or a maximum gradient detection algorithm applied to either of said sensitivity singularity or said phase singularity, or to a combination of both sensitivity and phase singularities.

15. A method of internal MRI employing at least one active internal MRI detector located within a sample of interest, comprising:
  applying an MRI pulse sequence to said sample of interest which includes said at least one active internal MRI detector, said MRI pulse sequence comprising spatial encoding projections;
  receiving MRI signals at the at least one active internal MRI detector;
  reconstructing at least one MRI image from the MRI signals using an error minimizing algorithm; and
  performing motion correction to said at least one MRI image,
  wherein said MRI pulse sequence provides an increase in an acquisition speed when reconstructing said at least one MRI image by sparsely under-sampling an image k-space in at least one dimension,
  wherein performing motion correction comprises reconstructing said MRI image from a viewpoint of said at least one active internal MRI detector at a center of a MRI field of view,
  wherein, in at least one spatially-encoding projection excited by said MRI pulse sequence, an MRI signal of said detector exhibits at least one singularity in a vicinity of a location of said at least one active internal MRI detector,
  wherein a location of the singularity is detected in said at least one projection using a detection algorithm,
  wherein the location of the singularity is used to determine whether said at least one projection has been corrupted by motion, and
  wherein said at least one projection is discarded and reacquired if it has been corrupted by motion.

16. An MRI scanner comprising a magnet system, an MRI detection system, and a data acquisition system,
  wherein said data acquisition system is configured to perform accelerated high-resolution internal MRI with a single active internal MRI detector, and an MRI pulse sequence in which an image projection is acquired in at least one spatial dimension,
  wherein at least one image is reconstructed by using an error minimization algorithm, said error minimizing algorithm being a compressed sensing error minimization algorithm, and
  wherein said MRI pulse sequence provides an increase in an acquisition speed when reconstructing said at least one image by sparsely under-sampling an image k-space in at least one dimension.

17. An MRI scanner comprising a magnet system, an MRI detection system, and a data acquisition system,
  wherein said data acquisition system is configured to perform accelerated high-resolution internal MRI with at least one active internal MRI detector, and an MRI pulse sequence in which an image projection is acquired in at least one spatial dimension,
  wherein at least one image is reconstructed by using an error minimization algorithm,
  wherein said MRI pulse sequence provides an increase in an acquisition speed when reconstructing said at least one image by sparsely under-sampling an image k-space in at least one dimension,
  wherein said data acquisition system is further configured to provide reduced motion sensitivity,
  wherein, in at least one projection, the MRI signal of said detector exhibits at least one singularity in the vicinity of the location of said MRI detector,
  wherein the location of the singularity is detected in said at least one projection using a singularity detection algorithm,
  wherein the projection is shifted to the center of the image field of view, and
  wherein an image incorporating said at least one projection is reconstructed and displayed.

18. An MRI scanner comprising a magnet system, an MRI detection system, and a data acquisition system,
  wherein said data acquisition system is configured to perform accelerated high-resolution internal MRI with at least one active internal MRI detector, and an MRI pulse sequence in which an image projection is acquired in at least one spatial dimension,
  wherein at least one image is reconstructed by using an error minimization algorithm,
  wherein said MRI pulse sequence provides an increase in an acquisition speed when reconstructing said at least one image by sparsely under-sampling an image k-space in at least one dimension,
  wherein said data acquisition system is further configured to provide reduced motion sensitivity,
  wherein, in at least one projection, the MRI signal of said detector exhibits at least one singularity in the vicinity of the location of said MRI detector,
  wherein the location of the singularity is detected in said at least one projection using a singularity detection algorithm,
  wherein the location of the singularity is used to determine whether said at least one projection has been corrupted by motion;
  wherein said at least one projection is discarded and reacquired if it has been corrupted by motion and,
  wherein an image incorporating said at least one projection is reconstructed and displayed.

19. A single active MRI detector for performing internal MRI in a sample of interest wherein an MRI pulse sequence is applied and an image projection is acquired in at least one spatial dimension,
  wherein the MRT properties of the single detector are such that in at least one projection the MRI signal of the single detector exhibits at least one singularity in the vicinity of its location, and
  wherein the singularity involves at least one of the sensitivity of the single detector undergoes a transition from substantially an MRI signal maximum immediately adjacent to said single MRI detector to substantially a signal void at the location of the single detector itself is substantially voided; or the phase of the single detector undergoes a substantial reversal from at least at one location adjacent to the said single MRI detector as compared to a location diametrically opposite to said at least one adjacent location, and
  wherein MRI signals are received and an MRI image is reconstructed using a compressed sensing error minimization algorithm to provide an increase in an acquisition speed when said MRI image is sparsely undersampled in image k-space in at least one dimension.

20. A method of internal MRI employing a single active internal MRI detector located within a sample of interest, comprising:
applying an MRI pulse sequence to said sample of interest which includes said single active internal MRI detector, wherein said MRI pulse sequence excites at least one spatial projection of the sample;
receiving MRI signals at the single active internal MRI detector; and
reconstructing at least one MRI image from the MRI signals,
wherein, in the least one spatially-encoding projection, an MRI signal of said single detector exhibits at least one singularity in a vicinity of a location of said single internal MRI detector,
wherein a location of the singularity is detected in said at least one projection using a detection algorithm, and
wherein the projection is shifted to the center of the MRI field of view prior to image reconstruction.

21. The method of claim 20, wherein the at least one singularity is defined as one or more points in the projection where one of a sensitivity of the single detector undergoes a transition from substantially an MRI signal maximum immediately adjacent to said single MRI detector to substantially a signal void at the location of the single detector, or a phase of the single detector undergoes a substantial reversal from at least at one location adjacent to said single MRI detector as compared to a location diametrically opposite to said at least one adjacent location.

22. The method of claim 21, wherein said MRI pulse sequence generates a stream of spatially-encoding projections wherein singularities are detected,
wherein each projection is shifted to the center of the field of view thereby creating a set of such spatially shifted projections, and
wherein at least one image is reconstructed from said set of projections.

23. The method of claim 22, wherein the MRI pulse sequence is applied repeatedly and multiple images reconstructed to form a cine stream with said detector always positioned substantially at the center of the image field of view.

24. The method of claim 23, wherein said cine stream is created by successively replacing the oldest acquired of said spatially-encoding projection of the MRI sequence with the most recently acquired spatially-encoding projection.

25. The method of claim 21, wherein said detection algorithm is at least one of a cross-correlation algorithm or a maximum gradient detection algorithm applied to either of said sensitivity singularity or said phase singularity, or to a combination of both sensitivity and phase singularities.

* * * * *